Jan. 13, 1948. L. M. TOMS Plant Pat. 779

RASPBERRY PLANT

Filed Sept. 26, 1946 2 Sheets-Sheet 1

Jan. 13, 1948. L. M. TOMS Plant Pat. 779

RASPBERRY PLANT

Filed Sept. 26, 1946 2 Sheets-Sheet 2

Inventor:
L. M. Toms

By: Robert Cobb
Attorneys.

Patented Jan. 13, 1948

Plant Pat. 779

UNITED STATES PATENT OFFICE

779

RASPBERRY PLANT

Lawrence Marston Toms, Nevada, Iowa, assignor to Inter-State Nurseries, Hamburg, Iowa Application September 26, 1946, Serial No. 699,472

1 Claim. (Cl. 47—62)

The present invention relates to a new and distinct variety of raspberry plant, resulting from the crossing of the two known varieties "Latham" and "Plum Farmer." As is well known, the "Latham" is a red variety, while the "Plum Farmer" is a black variety. From such a cross, the progeny would be expected to fall in the purple raspberry class, rather than in the black or red.

This new variety has a number of very important distinctive characteristics, combined with the color character, such as its habit of producing unusually long fruiting stems reducing labor of picking; its extreme disease resistance; prolific bearing of large berries of fine quality and bright red color over a long period of time; and hardiness or extreme resistance to cold snaps in the spring of the year.

Referring to certain of these novel features, it is notable that the new canes, after they reach the height of four or five feet, then stop growing, unlike the habit of other varieties which continue to grow and thus necessitate cutting back. The fruiting stems come out from almost the entire length of these canes. At the top, the stems are 6 to 8 inches in length and near the bottom they are sometimes 15 to 18 inches long.

As to disease resistance, the present variety was grown in the same field under comparable conditions with different varieties of red raspberries, including the parent "Latham," "Chief," and "Indian Summer," and all of the other varieties showed disease while the new variety (unsprayed) showed no signs of disease. This resistance to disease is not the usual characteristic of other varieties of red raspberries.

In comparison with the parent variety "Latham," the canes of the new variety do not grow as tall; produce more heavily and over a longer period of time; the fruit is of better quality, not quite as large, and perhaps not as firm.

Figure 1:
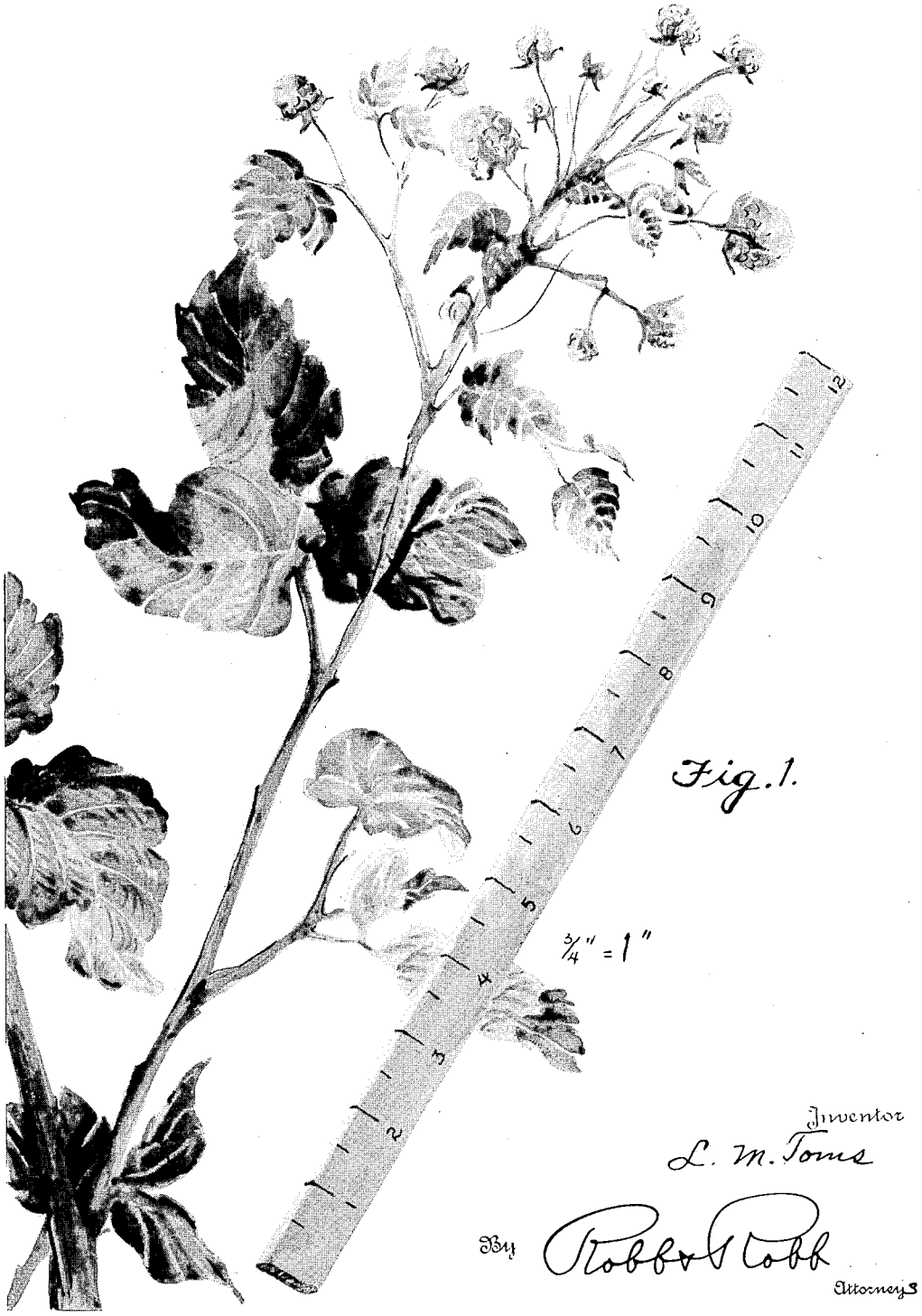
Figure 2:
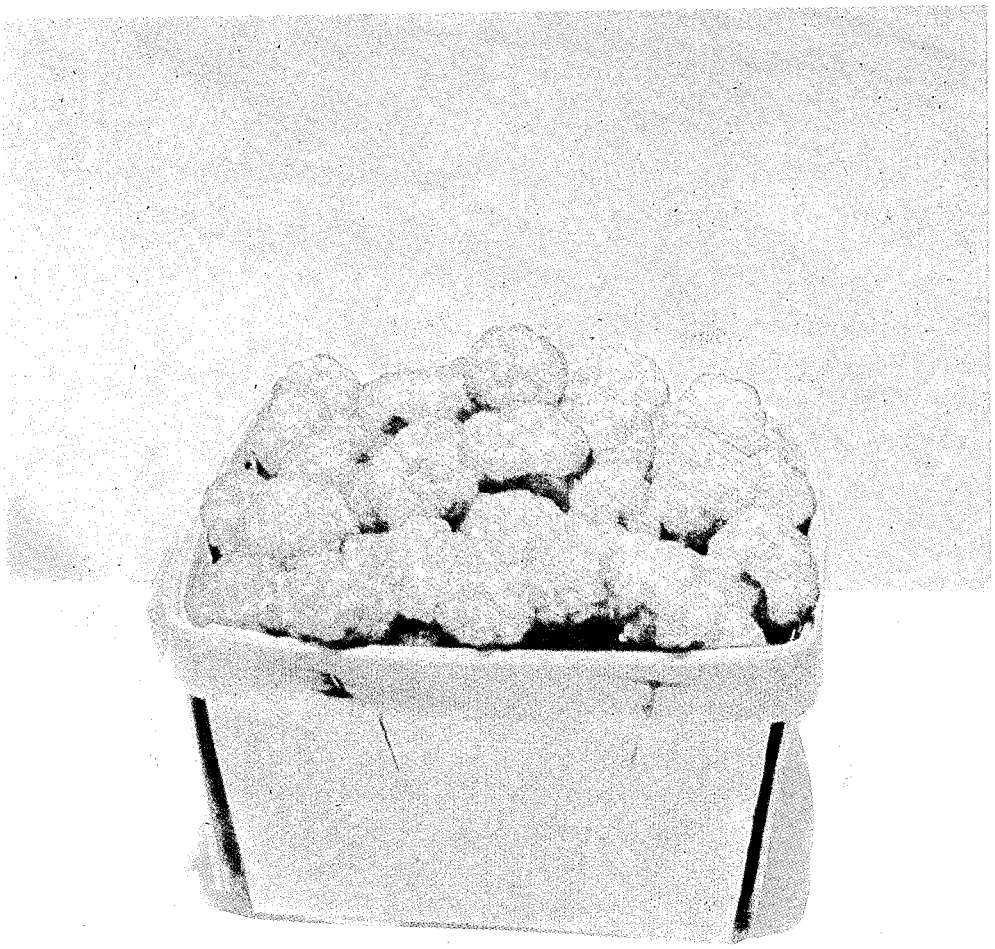

Figure 1 of the drawings shows an average fruiting stem in comparison with a 12 inch rule, on a scale of ¾ inch to 1 inch, and Figure 2 is a perspective view of a container filled with the bright red fruit of this new variety.

The following description specifically sets forth the characteristics of this new variety of red raspberry, all references to color according with the common dictionary definition.

Asexual reproduction proves these characteristics hold through succeeding propagations.

Specimens described grown at Nevada, Iowa.

First picking begins latter part of June and lasts to August 1st, in the above mentioned location.

Plant:
- *Growth.*—Medium; upright.
- *Root.*—Vigorous.
- *Crown.*—Branched; medium.
- *Canes.*—Unbranched; medium stout.

Leaves:
- *Number and size.*—Many; medium size; pinnately 5 foliate.
- *Petiole.*—Long; stout.
- *Color.*—Dark green.
- *Bracts.*—Absent.
- *Pubescence.*—Wanting.
- *Groove.*—Shallow; longer than that of the lateral.
- *Blade central leaflet.*—Exceeds lateral.
- *Serrations.*—Irregular; teeth broadly ovate; broadly cut serrate; glabrous on margin; apex green; those of central leaflet extend over three-fourths of margin and on outer margin of lateral leaflets nearly to base.
- *Leaflet surface.*—Upper—dull; flat; curled; dark green color. Lower—Pale green.
- *Younger foliage.*—Somewhat curled; inclined to cluster near tip late in season.

Flower stems: Long; inflorescence. Exposed, covered with setiform prickles.

Bloom: Early; date of first bloom, May 8–10; date of full bloom, June 1st.
- *Flowers.*—Many.
- *Breadth primary and secondary.*—¼ inch; perfect.
- *Filaments of stamens.*—Medium.
- *Pollen.*—Medium.
- *Fruiting stems.*—Very long; medium stout; decumbent.
- *Branches of truss.*—Many.

Soil where grown: Loamy, well drained.

Culture: Moderate early in growing season, never sprayed.

Disease resistance:
- *Plant.*—Extremely good; never shown any signs of disease.
- *Fruit.*—Good.

Insect resistance: Plant—good.

Frost resistance: Good.
Drouth resistance: Good.
Fruit: Condition when described—prime to overripe. Date described—July 27, 1946.

*Size.*—Uniform, large; constant throughout. Average fruit length—¾ inch; breadth—¾ inch; thickness—⅝ inch.

*Form.*—Uniform; regular; globose. Apex—rounded.

*Stems.*—Slender, long. Pubescence—wanting. Main truss-slender.

*Surface.*—Glossy. Color—bright red becoming darker when overripe. Drupelets—well developed; large; do not crumble readily.

*Core.*—Torus—small; enlarged sufficiently to prevent dropping of fruit when ripe.

*Flesh.*—Juicy. Color—dark red. Textile—medium firm; fine; melting.

*Flavor.*—Subacid; rich.

*Quality.*—Best. Shipping quality—fair.

*Use.*—Local, canning, dessert.

I claim:

A new and distinct variety of raspberry plant, characterized as to novelty by the restricted growth of the canes; the habit of such canes of producing unusually long fruiting stems throughout the entire length thereof; hardiness and extreme resistance of the plant to disease; and prolific bearing of large berries of fine quality and bright red color, becoming darker when overripe, over a long period of time, substantially as shown and described.

LAWRENCE MARSTON TOMS.